United States Patent
Lizarzaburu Chavez

(10) Patent No.: US 10,463,006 B2
(45) Date of Patent: Nov. 5, 2019

(54) MELON VARIETY NUN 68106 MEM

(71) Applicant: NUNHEMS B.V., AB Nunhem (NL)

(72) Inventor: Juan Antonio Lizarzaburu Chavez, Cartagena—Murcia (ES)

(73) Assignee: NUNHEMS B.V., Nunhem (NL)

( * ) Notice: Subject to any disclaimer, the term of this patent is extended or adjusted under 35 U.S.C. 154(b) by 0 days.

(21) Appl. No.: 15/933,811

(22) Filed: Mar. 23, 2018

(65) Prior Publication Data

US 2018/0206444 A1  Jul. 26, 2018

(51) Int. Cl.
| | | |
|---|---|---|
| *A01H 5/10* | (2018.01) | |
| *A01H 6/34* | (2018.01) | |
| *A01H 4/00* | (2006.01) | |
| *A01H 1/02* | (2006.01) | |
| *A01H 5/08* | (2018.01) | |

(52) U.S. Cl.
CPC .............. *A01H 6/344* (2018.05); *A01H 1/02* (2013.01); *A01H 4/005* (2013.01); *A01H 5/08* (2013.01); *A01H 5/10* (2013.01)

(58) Field of Classification Search
None
See application file for complete search history.

(56) References Cited

U.S. PATENT DOCUMENTS

| | | |
|---|---|---|
| 2015/0126380 A1 | 5/2015 | Van Dun |
| 2015/0245570 A1 | 9/2015 | Vogelaar et al. |
| 2017/0071145 A1 | 3/2017 | Tadmor et al. |
| 2017/0240913 A1 | 8/2017 | Schaffer et al. |
| 2017/0335339 A1 | 11/2017 | Van Dun et al. |

FOREIGN PATENT DOCUMENTS

| | | |
|---|---|---|
| WO | 2013182646 A1 | 12/2013 |
| WO | 2014076249 A1 | 5/2014 |
| WO | 2015136532 A1 | 9/2015 |
| WO | 2016016855 A1 | 2/2016 |
| WO | 2016120438 A1 | 8/2016 |

OTHER PUBLICATIONS

Ren et al., "Shoot regeneration and ploidy variation in tissue culture of honeydew melon (*Cucumis melo* L *inodorus*)," In Vitro Cell. Dev.Biol.—Plant, vol. 49, pp. 223-229, 2013.

Colijn-Hooymans, J.C. et al., "Competence for regeneration of cucumber cotyledons is restricted to specific development stages," Plant Cell, Tissue and Organ Culture, vol. 39, pp. 211-217, 1994.

UPOV, "Guidelines for the Conduct of Tests for Distinctness, Uniformity and Stability, TG104/5 (Geneva 2006, as last revised in 2014)," http://www/upov.int/edocs/tgdocs/en/tg104.pdf.

USDA, "Objective Description of Variety—Muskmelon/Cantaloupe (*Cucumis melo* L.)," http://www.ams.usda.gov/sites/default/files/media/38-Muskmelon-Cantaloupe.pdf, Feb. 2006.

Vos et al., "AFLP: a new technique for DNA fingerprinting," Nucleic Acids Research, vol. 23, No. 21, pp. 4407-4414, 1995.

Parvathaneni et al., "Fingerprinting in Cucumber and Melon (*Cucumis* spp.) Genotypes Using Morphological and ISSR Markers," J. Crop Sci. Biotech, vol. 14, No. 1, pp. 39-43, Mar. 2011.

Wijnker et al, "Hybrid recreation by reverse breeding in *Arabidopsis thaliana*," Nature Protocols, vol. 9, No. 4, pp. 761-772, published online Mar. 6, 2014.

Martin et al., "Identification of markers linked to agronomic traits in globe artichoke," Australian Journal of Crop Science, vol. 1, No. 2, pp. 43-46, 2008.

*Primary Examiner* — Brent T Page

(74) *Attorney, Agent, or Firm* — Arent Fox LLP

(57) ABSTRACT

The invention provides a new and distinct hybrid variety of melon, NUN 68106 MEM as well as seeds and plants and fruits thereof.

24 Claims, No Drawings

MELON VARIETY NUN 68106 MEM

FIELD OF THE INVENTION

The present invention relates to the field of plant breeding and, more specifically, to the development of NUN 68106 MEM (also designated as NUN 68106 or NUN 68106 F1 or NUN 68106 hybrid). The invention further relates to vegetative reproductions of NUN 68106 MEM, methods for tissue culture of NUN 68106 MEM and regenerating a plant from such a tissue culture and also to phenotypic variants of NUN 68106 MEM.

The goal of vegetable breeding is to combine various desirable traits in a single variety/hybrid. Such desirable traits may include greater yield, resistance to diseases, insects or other pests, tolerance to heat and drought, better agronomic quality, higher nutritional value, enhanced growth rate and improved fruit properties.

Breeding techniques take advantage of a plant's method of pollination. There are two general methods of pollination: a plant self-pollinates if pollen from one flower is transferred to the same or another flower of the same genotype. A plant cross-pollinates if pollen comes to it from a flower of a different genotype.

Plants that have been self-pollinated and selected for (uniform) type over many generations become homozygous at almost all gene loci and produce a uniform population of true breeding progeny of homozygous plants. A cross between two such homozygous plants of different lines produces a uniform population of hybrid plants that are heterozygous for many gene loci. The extent of heterozygosity in the hybrid is a function of the genetic distance between the parents. Conversely, a cross of two plants each heterozygous at a number of loci produces a segregating population of hybrid plants that differ genetically and are not uniform. The resulting non-uniformity makes performance unpredictable.

The development of uniform varieties requires the development of homozygous inbred plants, the crossing of these inbred plants to make hybrids, and the evaluation of the hybrids resulting from the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines are developed by selfing and selection of desired phenotypes. The new plants are evaluated to determine which have commercial potential. One crop species which has been subject to such breeding programs and is of particular value is the melon.

One crop species which has been subject to such breeding programs and is of particular value is the melon. It is a member of the Cucurbitacea family. The genus *Cucumis melo* originated in Africa. The plant is a large and sprawling annual, grown for its fruit. The fruit of most species of *Cucumis melo* is often coloured attractively, commonly red, orange or yellow. Melon can contain black seeds, which are considered undesirable for certain uses.

Many different melon cultivars have been produced, and melon breeding efforts have been underway in many parts of the world. Some breeding objectives include varying the color, texture and flavor of the fruit, and absence of seeds. Other objectives include disease or pest resistance, optimizing flesh thickness, yield, suitability to various climatic circumstances, solid content (% dry matter), and sugar content.

SUMMARY OF THE INVENTION

In an aspect of the invention, a seed of melon variety NUN 68106 MEM is provided, wherein a representative sample of said seed will be deposited under Accession Number NCIMB 42990. The invention also provides for a plurality of seeds of NUN 68106 MEM. The melon seed of NUN 68106 MEM may be provided as an essentially homogeneous population of melon seed. Therefore, seed of the invention may be defined as forming at least about 97% of the total seed, including at least about 98%, 99% or more of the seed. The population of seed of NUN 68106 MEM may be particularly defined as being essentially free from other seed. The seed population may be grown into plants to provide an essentially homogeneous population of melon plants according to the invention.

Also encompassed are a plant grown from a seed of melon variety NUN 68106 MEM and a plant part thereof. In another aspect the invention provides for a hybrid variety of melon called NUN 68106 MEM. The invention also provides for a progeny of NUN 68106 MEM. Especially, a plant or a progeny retaining all or all but one, two or three of the "distinguishing characteristics" or all or all but one, two or three of the "morphological and physiological characteristics" of NUN 68106 MEM referred to herein, is encompassed herein as well as methods for producing that plant or progeny.

In one aspect, a plant or a progeny of the invention have all the physiological and morphological characteristics of variety NUN 68106 MEM when grown under the same environmental conditions. In another aspect such a plant or such progeny have all or all but one, two or three of the physiological and morphological characteristics of NUN 68106 MEM when measured under the same environmental conditions and evaluated at significance levels of 1%, 5% or 10% significance (which can also be expressed as a p-value) wherein a representative sample of seed of variety NUN 68106 MEM has been deposited under Accession Number NCIMB 42990. In a second aspect, a plant or a progeny of the invention have all the physiological and morphological characteristics of variety NUN 68106 MEM when grown under the same environmental conditions. In another aspect such a plant or such progeny have all or all but one, two or three of the physiological and morphological characteristics as listed in Table 1 for variety NUN 68106 MEM when measured under the same environmental conditions and evaluated at significance levels of 1%, 5% or 10% significance.

In another aspect a plant of NUN 68106 MEM or said progeny plants has 3, 4, or more or all of the distinguishing characteristics which are different from the reference variety: 1) Shelf life of fruit; 2) resistance to *Fusarium oxysporum* f.sp. *melonis* race 2; 3) resistance to *Spaerotheca fuliginea* (*Podospaera xanthii*) (Powdery mildew) race 5. NUN 68106 MEM is a Piel de Sapo melon.

Also a plant part obtained from variety NUN 68106 MEM is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. In a further embodiment, the plant part obtained from variety NUN 68106 MEM is a cell, optionally a cell in a cell or tissue culture. That cell may be grown into a plant of NUN 68106 MEM.

The invention also provides a cell culture of NUN 68106 MEM and a plant regenerated from NUN 68106 MEM, which plant has all the characteristics of NUN 68106 MEM when grown under the same environmental conditions, as well as methods for regenerating NUN 68106 MEM. Alternatively, a regenerated plant may have one characteristic that is different from NUN 68106 MEM.

Further, a vegetatively propagated plant of variety NUN 68106 MEM is provided having all or all but one, two or three of the morphological and physiological characteristics NUN 68106 MEM when grown under the same environmental conditions.

Further, a melon fruit produced on a plant grown from a seed of NUN 68106 MEM is provided. Such a fruit can be consumed directly or processed into a food product.

In still another aspect, a seed growing or grown on a plant of NUN 68106 MEM is provided (i.e. produced after pollination of the flower of NUN 68106 MEM).

DEFINITIONS

All patent and non-patent documents cited herein are incorporated by reference in their entirety "Melon" or "muskmelon" refers herein to plants of the species Cucumis melo, and fruits thereof. The most commonly eaten part of a melon is the fruit or berry, also known as pepo. The fruit comprises exocarp, mesocarp, endocarp or seed cavity, hypanthium tissue and optionally seed. exocarp, mesocarp, endocarp or seed cavity, hypanthium tissue, and seedcoat of the seed are maternal tissues, so they are genetically identical to the plant on which they grow.

"Cultivated melon" refers to plants of Cucumis melo i.e. varieties, breeding lines or cultivars of the species C. melo as well as crossbreds thereof, or crossbreds with other Cucumis melo species, or even with other Cucurbitacea species, cultivated by humans and having good agronomic characteristics; preferably such plants are not "wild plants", i.e. plants which generally have much poorer yields and poorer agronomic characteristics than cultivated plants and e.g. grow naturally in wild populations. "Wild plants" include for example ecotypes, PI (Plant Introduction) lines, landraces or wild accessions or wild relatives of Cucumis melo and related species.

"Piel de Sapo melon" or "Santa Claus Melon" refers to melons with a rough mottled rind resembling toad skin, with an oval shape.

The terms "melon plant designated NUN 68106 MEM", "NUN 68106 MEM", "NUN 68106", "NUN 68106 F1", "68106 MEM" or "melon 68106" are used interchangeably herein and refer to a melon plant of variety NUN 68106 MEM, representative seed of which having been deposited under Accession Number NCIMB 42990.

A "seed of NUN 68106 MEM" refers to a melon seed which can be grown into a plant of NUN 68106 MEM wherein a representative sample of viable seed of NUN 68106 MEM has been deposited under Accession Number NCIMB 42990. A seed can be in any stage of maturity, for example a mature, viable seed, or an immature, non-viable seed. A seed comprises an embryo and maternal tissues.

An "embryo of NUN 68106 MEM" refers to an "F1 hybrid embryo" as present in a seed of NUN 68106 MEM, a representative sample of said seed of NUN 68106 MEM having been deposited under Accession Number NCIMB 42990.

A "seed grown on NUN 68106 MEM" refers to a seed grown on a mature plant of NUN 68106 MEM or inside a fruit of NUN 68106 MEM. The "seed grown on NUN 68106 MEM" contains tissues and DNA of the maternal parent, NUN 68106 MEM. The "seed grown on NUN 68106 MEM" contains an F2 embryo. When said seed is planted, it grows into a first generation progeny plant of NUN 68106 MEM.

A "fruit of NUN 68106 MEM" refers to a fruit containing maternal tissues of NUN 68106 MEM as deposited under Accession Number NCIMB 42990. In one option, the fruit contains seed grown on NUN 68106 MEM. In another option, the fruit does not contain seed, so the fruit is parthenocarpic. The skilled person is familiar with methods for inducing parthenocarpy. Those methods comprise chemically or genetically inducing parthenocarpy. Compounds suitable for chemically inducing parthenocarpy comprise auxins, gibberellins and cytokinins. Methods for genetically inducing parthenocarpy comprise the methods described in WO2016120438, WO2016016855, and WO2015136532). A fruit can be in any stage of maturity, for example a mature fruit in the yellow stage comprising viable seed, or an immature fruit in the edible green stage comprising non-viable seed.

"Tissue culture" refers to a composition comprising isolated cells of the same or a different type or a collection of such cells organized into parts of a plant. Tissue culture of various tissues of melon and regeneration of plants therefrom is well known and widely published (see, e.g., Ren et al., In Vitro Cell. Dev. Biol. —Plant (2013) 49:223-229; Colijn-Hooymans (1994), Plant Cell, Tissue and Organ Culture 39: 211-217). Similarly, the skilled person is well-aware how to prepare a "cell culture".

"UPOV descriptors" are the plant variety descriptors described for melon in the "Guidelines for the Conduct of Tests for Distinctness, Uniformity and Stability, TG104/5 (Geneva, as last revised in 2014), as published by UPOV (International Union for the Protection of New Varieties and Plants, available on the world wide web at upov.int) and which can be downloaded from the world wide web at upov.int/under edocs/tgdocs/en/tg104.pdf and is herein incorporated by reference in its entirety.

"RHS" refers to the Royal Horticultural Society of England which publishes an official botanical color chart quantitatively identifying colors according to a defined numbering system. The chart may be purchased from Royal Horticulture Society Enterprise Ltd RHS Garden; Wisley, Woking; Surrey GU236QB, UK, e.g., the RHS color chart: 2007 (The Royal Horticultural Society, charity No: 222879, PO Box 313 London SW1P2PE.

As used herein and except as otherwise indicated, the term "plant" includes the whole plant or any part thereof, preferably having the same genetic makeup as the plant from which it is obtained, such as a plant organ (e.g. harvested or non-harvested fruits), a plant cell, a plant protoplast, a plant cell tissue culture or a tissue culture from which a whole plant can be regenerated, a plant cell that is intact in a plant, a clone, a micropropagation, plant callus, a plant cell clump, a plant transplant, a vegetative propagation, a seedling, or parts of a plant (e.g. harvested tissues or organs), such as a fruit, a harvested fruit, a part of a fruit, a leaf, a part of a leaf, pollen, an ovule, an embryo, a petiole, a shoot or a part thereof, a stem or a part thereof, a root or a part thereof, a root tip, a cutting, a seed, a part of a seed, seed coat or another maternal tissue which is part of a seed grown on a variety of the invention, hypocotyl, cotyledon, a scion, a graft, a stock, a rootstock, a pistil, an anther, and a flower or parts of any of these and the like. Also any developmental stage is included, such as seedlings, cuttings prior or after rooting, mature plants or leaves. Alternatively, a plant part may also include a plant seed which comprises one or two sets of chromosomes derived from the parent plant, e.g. from NUN 68106 MEM. An F2 progeny produced from self-pollination of NUN 68106 MEM will thus comprise two sets of chromosomes derived from NUN 68106 MEM, while an F2 progeny derived from cross-fertilization of NUN 68106 MEM will comprise only one set of chromosomes from NUN 68106 MEM and the other set of chromosomes from the other parent.

"Harvested plant material" refers herein to plant parts (e.g. fruits detached from the whole plant) which have been collected for further storage and/or further use.

"Reference Variety" or "check variety" refers herein to variety Jimenado F1, a commercial variety from company Syngenta, which can planted in a trial together with NUN 68106 MEM.

"Rootstock" or "stock" refers to the plant selected for its roots, in particular for the resistance of the roots to diseases or stress (e.g. heat, cold, salinity etc.). Normally the quality of the fruit of the plant providing the rootstock is less important.

"Scion" refers to a part of the plant that is attached to the rootstock. This plant is selected for its stems, leaves, flowers, or fruits. The scion contains the desired genes to be duplicated in future production by the stock/scion plant and may produce the desired melon fruit.

"Stock/scion" or grafted plant refers to a melon plant comprising a rootstock from one plant grafted to a scion from another plant.

A plant having "all the physiological and morphological characteristics" of a referred-to-plant means a plant showing the physiological and morphological characteristics of the referred-to-plant when grown under the same environmental conditions, preferably in the same experiment; the referred-to-plant can be a plant from which it was derived, e.g. the progenitor plant, the parent, the recurrent parent, the plant used for tissue- or cell culture, etc. A physiological or morphological characteristic can be a numerical characteristic or a non-numerical characteristic. In one aspect, a plant has "all but one, two or three of the physiological and morphological characteristics" of a referred-to-plant, or "all the physiological and morphological characteristics" of Table 1 or "all or all but one, two or three of the physiological and morphological characteristics" of Table 1.

The physiological and/or morphological characteristics mentioned above are commonly evaluated at significance levels of 1%, 5% or 10% if they are numerical, or for having an identical degree (or type) if not numerical, if measured under the same environmental conditions. For example, a progeny plant or a Single Locus Converted plant or a mutated plant of NUN 68106 MEM may have one or more (or all) of the essential physiological and/or morphological characteristics of said variety listed in Table 1, as determined at the 5% significance level (i.e. $p<0.05$) when grown under the same environmental conditions.

"Distinguishing characteristics" or "distinguishing morphological and/or physiological characteristics" refers herein to the characteristics which distinguish (i.e. are different) between the new variety and other melon varieties, such as the Reference Variety, when grown under the same environmental conditions. The distinguishing characteristics between NUN 68106 MEM and Reference Variety are described elsewhere herein and also can be seen in Table 1. When comparing NUN 68106 MEM with different varieties, the distinguishing characteristics will be different. In one aspect, the distinguishing characteristics may therefore include at least one, two, three or more (or all) of the characteristics listed in Table 1. All numerical distinguishing characteristics are statistically significantly different at $p<0.05$ between NUN 68106 MEM and the other variety, e.g. Reference Variety.

NUN 68106 MEM has the following distinguishing characteristics when compared to the Reference Variety: 1) Shelf life of fruit; 2) resistance to *Fusarium oxysporum* f.sp. *melonis* race 2; 3) resistance to *Spaerotheca fuliginea* (*Podospaera xanthii*) (Powdery mildew) race 5. This can be seen in for example Table 1, where the characteristics of NUN 68106 MEM are listed for comparison to the characteristics of Reference Variety.

Thus, a melon plant "comprising the distinguishing characteristics of NUN 68106 MEM (such as a progeny plant) refers herein to a plant which does not differ significantly from said variety in the distinguishing characteristics above. Therefore in one aspect a plant (such as a progeny plant of NUN 68106 MEM) is provided which does not differ significantly from NUN 68106 MEM in the distinguishing characteristics above.

Similarity and differences between two different plant lines or varieties can be determined by comparing the number of morphological and/or physiological characteristics (e.g. the characteristics as listed in Table 1) that are the same (i.e. statistically not significantly different) or that are different (i.e. statistically significantly different) between the two plant lines or varieties when grown under the same environmental conditions. A numerical characteristic is considered to be "the same" when the value for a numeric characteristic is not significantly different at the 1% ($p<0.01$) or 5% ($p<0.05$) significance level, using one way Analysis of variance (ANOVA), a standard method known to the skilled person. Non-numerical or "degree" or "type" characteristic are considered "the same" when the values have the same "degree" or "type" when scored using UPOV descriptors, if the plants are grown under the same environmental conditions.

As used herein, the term "variety", "cultivated melon" or "cultivar" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

A "plant line" is for example a breeding line which can be used to develop one or more varieties. A breeding line is typically highly homozygous.

"Hybrid variety" or "F1 hybrid" refers to the seeds harvested from crossing two inbred (nearly homozygous) parental lines. For example, the female parent is pollinated with pollen of the male parent to produce hybrid (F1) seeds on the female parent.

"Regeneration" refers to the development of a plant from cell culture or tissue culture or vegetative propagation.

"Vegetative propagation", "vegetative reproduction" or "clonal propagation" are used interchangeably herein and mean a method of taking a part of a plant and allowing that plant part to form at least roots, and also refer to the plant or plantlet obtained by that method. Optionally, the vegetative propagation is grown into a mature plant. The skilled person is aware of what plant parts are suitable for use in the method.

"Selfing" refers to self-pollination of a plant, i.e., the transfer of pollen from the anther to the stigma of the same plant.

"Crossing" refers to the mating of two parent plants. The term encompasses "cross-pollination" and "selfing".

"Cross-pollination" refers to the fertilization by the union of two gametes from different plants.

"Yield" means the total weight of all melon fruits harvested per hectare of a particular line or variety. It is understood that "yield" expressed as weight of all melon fruits harvested per hectare can be obtained by multiplying the number of plants per hectare times the "yield per plant". "Marketable yield" means the total weight of all marketable melon fruits, especially fruit that is not cracked, damaged or diseased, harvested per hectare of a particular line or variety.

As used herein, the terms "resistance" and "tolerance" are used interchangeably to describe plants that show no symptoms or significantly reduced symptoms to a specified biotic pest, pathogen, abiotic influence or environmental condition compared to a susceptible plant. These terms are optionally also used to describe plants showing some symptoms but that are still able to produce marketable product with an acceptable yield.

"Harvest maturity" is referred to as the stage at which a melon fruit is ripe or ready for harvest or the optimal time to harvest the fruit for the market, for processing or for consumption. In one embodiment, harvest maturity is the stage which allows proper completion of the normal ripening.

"Flavor" (or flavour) refers to the sensory impression of a food or other substance, especially a melon fruit or fruit part (fruit flesh) and is determined mainly by the chemical senses of taste and smell. Flavor is influenced by texture properties and by volatile and/or non-volatile chemical components (organic acids, lipids, carbohydrates, salts etc.).

"Aroma" refers to smell (or odor) characteristics of melon fruits or fruit parts (fruit flesh).

Refractometer % of soluble solids is the percentage of soluble solids in fruit juice, as defined by the USDA. It is also expressed as ° Brix and indicates sweetness. The majority of soluble solids in melon are mainly sugars present in the fruits of melon. Hence the correlation with sweetness. Brix can be measured using a Brix meter (also known as Refractometer).

The term "traditional breeding techniques" encompasses herein crossing, selfing, selection, doubled haploid production, embryo rescue, protoplast fusion, marker assisted selection, mutation breeding etc. as known to the breeder (i.e. methods other than genetic modification/transformation/transgenic methods), by which, for example, a genetically heritable trait can be transferred from one melon line or variety to another. It optionally includes epigenetic modifications.

"Backcrossing" is a traditional breeding technique used to introduce a trait into a plant line or variety. The plant containing the trait is called the donor plant and the plant into which the trait is transferred is called the recurrent parent. An initial cross is made between the donor parent and the recurrent parent to produce a progeny plant. Progeny plants which have the trait are then crossed to the recurrent parent. After several generations of backcrossing and/or selfing the recurrent parent comprises the trait of the donor. The plant generated in this way may be referred to as a "single trait converted plant". The technique can also be used on a parental line of a hybrid.

"Progeny" as used herein refers to a plant obtained from a plant designated NUN 68106 MEM. A progeny may be obtained by regeneration of cell culture or tissue culture or parts of a plant of said variety or selfing of a plant of said variety or by producing seeds of a plant of said variety. In further embodiments, progeny may also encompass plants obtained from crossing of at least one plant of said variety with another melon plant of the same variety or another variety or (breeding) line, or with wild melon plants. A progeny may comprise a mutation or a transgene. A first generation progeny" or is the progeny directly derived from, obtained from, obtainable from or derivable from the parent plant by, e.g., traditional breeding methods (selfing and/or cross-pollinating) or regeneration. Thus, a plant of NUN 68106 MEM is the male parent, the female parent or both of a first generation progeny of NUN 68106 MEM. Progeny may have all the physiological and morphological characteristics of variety NUN 68106 MEM when grown under the same environmental conditions and/or progeny may have (be selected for having) one or more of the distinguishing characteristics of melon of the invention. Using common breeding methods such as backcrossing or recurrent selection, one or more specific characteristics may be introduced into said variety, to provide or a plant comprising all but 1, 2, or 3 or more of the morphological and physiological characteristics of NUN 68106 MEM (as listed in Table 1)

The terms "gene converted" or "conversion plant" or "single locus converted plant" in this context refer to melon plants which are developed by backcrossing wherein essentially all of the desired morphological and physiological characteristics of the parent variety or line are recovered, in addition to the one or more genes transferred into the parent via the backcrossing technique (optionally including reverse breeding or reverse synthesis of breeding lines) or via genetic engineering or through mutation breeding. Likewise a "Single Locus Converted (Conversion) Plant" refers to plants which are developed by plant breeding techniques comprising or consisting of mutation and/or by genetic transformation and/or by backcrossing, wherein essentially all of the desired morphological and physiological characteristics of a melon variety are recovered in addition to the characteristics of the single locus having been transferred into the variety via the backcrossing technique. In case of a hybrid, the gene may be introduced in the male or female parental line.

"Marker" refers to a readily detectable phenotype, preferably inherited in codominant fashion (both alleles at a locus in a diploid heterozygote are readily detectable), with no environmental variance component, i.e., a heritability of 1.

"Average" refers herein to the arithmetic mean.

The term "mean" refers to the arithmetic mean of several measurements. The skilled person understands that the appearance of a plant depends to some extent on the growing conditions of said plant. Thus, the skilled person will know typical growing conditions for melons described herein. The mean, if not indicated otherwise within this application, refers to the arithmetic mean of measurements on at least 10 different, randomly selected plants of a variety or line.

DETAILED DESCRIPTION

The present invention relates to a plant of NUN 68106 MEM wherein a representative sample of seeds of said variety was deposited under the Budapest Treaty, with Accession number NCIMB 42990.

The present invention also relates to a seed of melon variety, referred to as NUN 68106 MEM, wherein a representative sample of said seed was deposited under the Budapest Treaty, with Accession number NCIMB 42990.

In another aspect, the invention provides for a melon plant part of variety NUN 68106 MEM, preferably a fruit, a representative sample of seed from said variety has been deposited under the Budapest Treaty, with Accession number NCIMB 42990.

A seed of hybrid variety NUN 68106 MEM is obtainable by crossing the male parent of said variety with the female parent of said variety and harvesting the seeds produced on the female parent. The resultant seeds of said variety can be grown to produce plants of said variety. In one embodiment a seed or a plurality of seeds of said variety are packaged into a container of any size or type (e.g., bags, cartons, cans, etc.). The seed may be disinfected, primed and/or treated with various compounds, such as seed coatings or crop protection compounds. The seed produces a plant of NUN 68106 MEM.

Also provided is a plant of melon variety NUN 68106 MEM, or a fruit or other plant part thereof, produced from a seed, wherein a representative sample of said seeds has been deposited under the Budapest Treaty, with Accession Number NCIMB 42990.

Also a plant part obtained from variety NUN 68106 MEM is provided, wherein said plant part is selected from the group consisting of: a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed coat or another maternal tissue which is part of a seed grown on said varieties, hypocotyl, cotyledon, a scion, a stock, a rootstock, a pistil, an anther, and a flower or a part thereof. Fruits are particularly important plant parts. Fruits may contain mature or immature and/or nonviable seeds. In a further embodiment, the plant part obtained from variety NUN 68106 MEM is a cell, optionally a cell in a cell or tissue culture. That cell may be grown into a plant of NUN 68106 MEM. A part of a variety of the invention, i.e. NUN 68106 MEM (or of progeny NUN 68106 MEM or of a plant having all physiological and/or morphological characteristics but one, two or three which are different from those of NUN 68106 MEM) further encompasses any cells, tissues, organs obtainable from the seedlings or plants in any stage of maturity.

The invention also provides for a food or feed product or a processed product comprising or consisting of a plant part described herein wherein the plant part can be identified as a part of the plant of the invention. Preferably, the plant part is a melon fruit or part thereof and/or an extract from a fruit or another plant part described herein comprising at least one cell of NUN 68106 MEM. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Such a plant part of NUN 68106 MEM can be stored and/or processed further. Encompassed are therefore also food or feed products comprising one or more of such parts, such as canned, chopped, diced, cooked, roasted, in a sauce, in a sandwich, pasted, puréed or concentrated, juiced, frozen, dried, pickled, or powdered melon fruit from NUN 68106 MEM or from progeny of said varieties, or from a derived variety, such as a plant having all but one, two or three physiological and/or morphological characteristics of NUN 68106 MEM.

In a preferred embodiment, the invention provides for a melon fruit of variety NUN 68106 MEM, or a part of a fruit of said varieties. The fruit can be in any stage of maturity, for example immature or mature. In another embodiment, the invention provides for a container comprising or consisting of a plurality of harvested melon fruits or parts of fruits of said variety, or fruits of progeny thereof, or fruits of a derived variety.

In another embodiment the plant, plant part or seed of NUN 68106 MEM is inside a container, For example, containers such as cans, boxes, crates, bags, cartons, Modified Atmosphere Packaging, films (e.g. biodegradable films), etc. comprising a plant or a part of a plant (fresh and/or processed) of NUN 68106 MEM or a seed of NUN 68106 MEM are also provided herein. In a preferred embodiment, the container comprises a plurality of seeds of NUN 68106 MEM, or a plurality of plant parts of NUN 68106 MEM.

The present invention further relates to a melon variety, referred to as NUN 68106 MEM, which—when compared to its REFERENCE VARIETY Jimenado F1—has the following distinguishing characteristics: 1) longer shelf life of fruit; 2) no resistance to *Fusarium oxysporum* f.sp. *melonis* race 2; 3) added resistance to *Spaerotheca fuliginea* (*Podospaera xanthii*) (Powdery mildew) race 5 where the characteristics are determined at the 5% significance level for plants grown under the same environmental conditions. Also encompassed by the present invention are parts of that plant.

In another embodiment NUN 68106 MEM has resistance to *Fusarium oxysporum* f.sp. *melonis* race 0 and 1 that is 9 (scale 1=absent, 9=present), to *Spaerotheca fuliginea* (*Podospaera xanthii*) (Powdery mildew) race 5 that is 3 (scale 1=susceptible, 9=highly resistant) and to Muskmelon Necrotic Spot Virus (MNSV) Race E8 that is 9 (scale 1=absent, 9=present) measured according to UPOV standards.

The invention further provides a melon plant which does not differ from the plant of NUN 68106 MEM as determined at the 1%, 2%, 3%, 4% or 5% significance level when grown under the same environmental conditions. Thus the plants are measured in the same trial. Preferably, the trial is conducted as recommended by the USDA or UPOV. The invention also comprises a part of said plant The invention also provides a tissue or cell culture comprising cells of NUN 68106 MEM. Such a tissue culture can for example be grown on plates or in liquid culture, or be frozen for long term storage. The cells of NUN 68106 MEM used to start the culture can be selected from any plant part suitable for vegetative reproduction, or in a preferred embodiment can be selected from embryos, meristems, cotyledons, hypocotyl, pollen, leaves, anthers, roots, root tips, pistil, petiole, flower, fruit, seed, stem and stalks of NUN 68106 MEM. In another preferred embodiment, the tissue culture does not contain somaclonal variation or has reduced somaclonal variation. The skilled person is familiar with methods to reduce or prevent somaclonal variation, including regular reinitiation.

In one embodiment the invention provides a melon plant regenerated from the tissue or cell culture of NUN 68106 MEM, wherein the regenerated plant is not significantly different from NUN 68106 MEM in all, or all but one, two or three, of the physiological and morphological characteristics (determined at the 5% significance level when grown under the same environmental conditions). Optionally, the plant has one, two or three the physiological and morphological characteristics that are affected by a mutation or by transformation. In another embodiment, the invention provides a melon plant regenerated from the tissue or cell culture of NUN 68106 MEM, wherein the plant has all of the physiological and morphological characteristics of said variety determined at the 5% significance level when grown under the same environmental conditions. In these cases, similarity or difference of a characteristic is determined by measuring the characteristics of a representative number of plants grown under the same environmental conditions, determining whether type/degree characteristics are the same or different and determining whether numerical characteristics are significantly different (determined at the 5% significance level).

A melon according to the invention, such as NUN 68106 MEM, or its progeny, or a plant having all physiological and/or morphological characteristics but one, two or three which are different from those of NUN 68106 MEM, can also be reproduced using vegetative reproduction methods. Therefore, the invention provides for a method of producing a plant, or a part thereof, of variety NUN 68106 MEM, comprising vegetative propagation of said variety. Vegetative propagation comprises regenerating a whole plant from a plant part of variety NUN 68106 MEM (or from a progeny of said variety or from or a plant having all physiological and/or morphological characteristics of said variety but one, two or three different characteristics), such as a cutting, a cell culture or a tissue culture.

The invention also concerns methods of vegetatively propagating a part of the plant of the invention NUN 68106 MEM. In certain embodiments, the method comprises the steps of: (a) collecting tissue or cells capable of being propagated from a plant of the invention; (b) cultivating said tissue or cells to obtain proliferated shoots; and (c) rooting said proliferated shoots, to obtain rooted plantlets. Steps (b) and (c) may also be reversed, i.e. first cultivating said tissue to obtain roots and then cultivating the tissue to obtain shoots, thereby obtaining rooted plantlets. The rooted plantlets may then be further grown, to obtain plants. In one embodiment, the method further comprises step (d) growing plants from said rooted plantlets. Therefore, the method also comprises regenerating a whole plant from said part of NUN 68106 MEM.

In a preferred embodiment, the part of the plant to be propagated is a cutting, a cell culture or a tissue culture.

The invention also provides for a vegetatively propagated plant of variety NUN 68106 MEM (or from progeny of said variety or from or a plant having all but one, two or three physiological and/or morphological characteristics of NUN 68106 MEM) wherein the plant has all of the morphological and physiological characteristics of NUN 68106 MEM when the characteristics are determined at the 5% significance level for plants grown under the same conditions. In another embodiment, the propagated plant has all but one, two or three of the morphological and physiological characteristics of NUN 68106 MEM when the characteristics are determined at the 5% significance level for plants grown under the same conditions. A part of said propagated plant or said propagated plant with one, two or three differences is also included.

In an embodiment, the invention provides a method for producing a melon plant part, preferably a fruit, comprising the steps of:
 a. Growing a plant of NUN 68106 MEM until it sets at least one fruit
 b. Collecting the fruit of step a)

Preferably, the fruit is collected at harvest maturity. In another embodiment, the fruit is collected when the seed is ripe. A plant of NUN 68106 MEM can be produced by seeding directly in the soil (e.g., field) or by germinating the seeds in controlled environment conditions (e.g., greenhouses) and optionally then transplanting the seedlings into the field. For example, the seed can be sown into prepared seed beds where they will remain for the entire production the crop. Alternatively, the melon seed may be planted through black plastic mulch. The dark plastic will absorb heat from the sun, warming the soil early. It will also help to conserve moisture during the growing season, controls weeds and makes harvesting easier and cleaner. Melon can also be grown entirely in greenhouses In still another aspect the invention provides a method of producing a melon plant, comprising crossing a plant of melon NUN 68106 MEM with a second melon plant at least once, allowing seed to develop and optionally harvesting said progeny seed. The skilled person can select progeny from said crossing. Optionally, the progeny is crossed twice, thrice, or four, five, six or seven times, and allowed to set seed. In one embodiment of the invention, the first step in "crossing" comprises planting seeds of a first and a second parent melon plant, often in proximity so that pollination will occur; for example, mediated by insect vectors. Alternatively, pollen can be transferred manually. Where the plant is self-pollinated, pollination may occur without the need for direct human intervention other than plant cultivation. After pollination the plant can produce seed.

In yet another aspect the invention provides a method of producing a plant, comprising selfing a plant of variety NUN 68106 MEM one or more times, and selecting a progeny plant from said selfing. In one aspect the progeny plant retains all the distinguishing characteristics of NUN 68106 MEM described above. In a different embodiment the progeny plant comprises all (or all but one, two or three) of the physiological and morphological characteristic of NUN 68106 MEM of Table 1. In a further embodiment the progeny plant comprises all physiological and morphological characteristic of NUN 68106 MEM when grown under the same environmental conditions.

In other aspects, the invention provides a progeny plant of variety NUN 68106 MEM such as a progeny plant obtained by further breeding that variety. Further breeding with the variety of the invention includes selfing that variety one or more times and/or cross-pollinating that variety with another melon plant or variety one or more times. In particular, the invention provides for a progeny plant that retains all the essential morphological and physiological characteristics of NUN 68106 MEM or, in another embodiment, a progeny plant that retains all, or all but one, two or three, of the morphological and physiological characteristics of NUN 68106 MEM, optionally all or all but one, two or three of the characteristics as listed in Table 1, when grown under the same environmental conditions, determined at the 5% significance level for numerical characteristics. In a preferred embodiment, the progeny is a first generation progeny, i.e. the ovule or the pollen (or both) used in the crossing is an ovule or pollen of variety NUN 68106 MEM, i.e. the pollen comes from an anther of NUN 68106 MEM and the ovule comes from an ovary of NUN 68106 MEM. In another aspect, the invention provides for a vegetative reproduction of the variety and a plant having all, or all but 1, 2, or 3 of the physiological and morphological characteristics of NUN 68106 MEM (e.g. as listed in Table 1).

The invention also provides a method for collecting pollen of NUN 68106 MEM, comprising the steps of:
 a. Growing a plant of NUN 68106 MEM until at least one flower contains pollen
 b. Collecting the pollen of step a)

Preferably, the pollen is collected when it is mature or ripe. A suitable method for collecting pollen comprises collecting anthers or the part of the anther that contains pollen, for example by cutting it off. Pollen can be collected in containers. Optionally, collected pollen can be used to pollinate a melon flower.

The morphological and/or physiological differences between two different individual plants of the invention (e.g. between NUN 68106 MEM and a progeny of NUN 68106 MEM) or between a plant of NUN 68106 MEM or progeny of said variety, or a plant having all, or all but 1, 2, or 3, of the physiological and morphological characteristics of NUN 68106 MEM (or all, or all but 1, 2, or 3 of the characteristics as listed in Table 1) and another known variety can easily be established by growing said variety next to each other or next to the other variety (in the same field, under the same environmental conditions), preferably in several locations which are suitable for said melon cultivation, and measuring morphological and/or physiological characteristics of a number of plants (e.g., to calculate an average value and to determine the variation range/uniformity within the variety). For example, trials can be carried out in Acampo Calif., USA (N 38 degrees 07'261"/W 121 degrees 18' 807", USA, whereby various characteristics, for example maturity, days from seeding to harvest, plant habit, plant attitude, leaf shape, leaf color, blistering, numbers of flowers per leaf axil, number of calyx lobes, number of petals, fruit group, immature fruit color, mature fruit color, pungency, flavor, fruit glossiness, fruit size, fruit shape, average number of fruits per plant, seed size, seed weight, anthocyanin level, disease resistance, insect resistance, can be measured and directly compared for species of melon. Thus, the invention comprises melon plant having one, two or three physiological and/or morphological characteristics which are different from those of the plant of NUN 68106 MEM and which otherwise has all the physiological and morphological characteristics of the plant of NUN 68106 MEM, when determined at the 5% significance level for plants grown under the same environmental conditions. In a preferred embodiment, the different characteristic is affected by a mutation, optionally induced mutation, or by transformation.

The morphological and physiological characteristics (and the distinguishing characteristics) of NUN 68106 MEM are provided in the Examples, in Table 1. Encompassed herein is also a plant obtainable from NUN 68106 MEM (e.g. by selfing and/or crossing and/or backcrossing with said variety and/or progeny of said variety) comprising all or all but one, two or three of the physiological and morphological characteristics of NUN 68106 MEM listed in Table 1 as determined at the 5% significance level for numerical characteristics or identical for non-numerical characteristics when grown under the same environmental conditions and/or comprising one or more (or all; or all except one, two or three) characteristics when grown under the same environmental conditions.

Also at-harvest and/or post-harvest characteristics of fruits can be compared, such as cold storage holding quality, post-harvest flesh firmness, and Brix can be measured using known methods. (Fruit) Flesh firmness can for example be measured using a penetrometer, e.g. by inserting a probe into the fruit flesh and determining the insertion force, or by other methods. Fruit flesh firmness can for example be measured using a "FT 327 Penetrometer", available from QA Supplies LLC, 1185 Pineridge Road, Norfolk, Va. 23502.

The morphological and/or physiological characteristics may vary somewhat with variation in the environment (such as temperature, light intensity, day length, humidity, soil, fertilizer use), which is why a comparison under the same environmental conditions is preferred. Colors can best be measured using the Royal Horticultural Society Chart (World Wide Web at rhs.org.uk/Plants/RHS-Publications/RHS-colour-charts).

In yet a further embodiment, the invention provides for a method of producing a new melon plant. The method comprises crossing a plant of the invention i.e. NUN 68106 MEM, or a plant comprising all but 1, 2, or 3 of the morphological and physiological characteristics of said variety (as listed in Table 1), or a progeny plant thereof, either as male or as female parent, with a second melon plant (or a wild relative of melon) one or more times, and/or selfing a melon plant according to the invention i.e. NUN 68106 MEM, or a progeny plant thereof, one or more times, and selecting progeny from said crossing and/or selfing. The second melon plant may for example be a line or variety of the species *Cucumis melo*, or other *Cucumis* species or other Cucurbitacea species.

The invention provides for methods of producing plants which retain all the morphological and physiological characteristics of a plant of the invention i.e. NUN 68106 MEM. The invention provides also for methods of producing a plant comprising all but 1, 2, or 3 or more of the morphological and physiological characteristics of NUN 68106 MEM (e.g. as listed in Table 1), but which are still genetically closely related to said variety. The relatedness can, for example be determined by fingerprinting techniques (e g, making use of isozyme markers and/or molecular markers such as Single-nucleotide polymorphism (SNP) markers, amplified fragment length polymorphism (AFLP) markers, microsatellites, minisatellites, Random Amplified Polymorphic DNA (RAPD) markers, restriction fragment length polymorphism (RFLP) markers and others). A plant is "closely related" to NUN 68106 MEM if its DNA fingerprint is at least 80%, 90%, 95% or 98% identical to the fingerprint of NUN 68106 MEM. In a preferred embodiment AFLP markers are used for DNA fingerprinting (Vos et al. 1995, Nucleic Acid Research 23: 4407-4414). A closely related plant may have a Jaccard's Similarity index of at least about 0.8, preferably at least about 0.9, 0.95, 0.98 or more (Parvathaneni et al., J. Crop Sci. Biotech. 2011 (March) 14 (1): 39~43).

The invention also provides a plant and a variety obtained or selected by applying these methods on NUN 68106 MEM. Such a plant may be produced by crossing and/or selfing, or alternatively, a plant may simply be identified and selected amongst plants of said variety, or progeny of said variety, e.g. by identifying a variant within NUN 68106 MEM or within progeny of said variety (e.g. produced by selfing) which variant differs from NUN 68106 MEM in one, two or three of the morphological and/or physiological characteristics (e.g. in one, two or three distinguishing characteristics), e.g. those listed in Table 1 or others. In one embodiment the invention provides a melon plant having a Jaccard's Similarity index with NUN 68106 MEM of at least 0.8, e.g. at least 0.85, 0.9, 0.95, 0.98 or even at least 0.99.

WO2013182646, which is incorporated by reference, relates to a non-destructive method for analyzing maternal DNA of a seed. In this method the DNA is dislodged from the seed coat surface and can be used to collect information on the genome of the maternal parent of the seed. This method for analyzing maternal DNA of a seed comprises the steps of contacting a seed with a fluid to dislodge DNA from the seed coat surface, and analyzing the DNA thus dislodged from the seed coat surface using methods known in the art. The skilled person is thus able to determine whether a seed has grown on a plant of a plant of the invention i.e. NUN 68106 MEM is a progeny of said variety, because the seed coat of the seed is a maternal tissue genetically identical to NUN 68106 MEM. In one embodiment, the present invention relates to a seed coat comprising maternal tissue of NUN 68106 MEM. In another embodiment the invention relates to a melon seed comprising a maternal tissue of NUN 68106 MEM.

By crossing and/or selfing also (one or more) single traits may be introduced into the variety of the invention i.e. NUN 68106 MEM (e.g., using backcrossing breeding schemes), while retaining the remaining morphological and physiological characteristics of said variety and/or while retaining one or more or all distinguishing characteristics. A single trait converted plant may thereby be produced. For example, disease resistance genes may be introduced, genes responsible for one or more quality traits, yield, etc. Both single genes (e.g. dominant or recessive) and one or more QTLs (quantitative trait loci) may be transferred into NUN 68106 MEM by breeding with said variety.

Alternatively, a single trait converted plant or single locus converted plant of NUN 68106 MEM may be produced by the following steps
 a. obtaining a cell or tissue culture of cells of NUN 68106 MEM;
 b. genetically transforming or mutating said cells;
 c. growing the cells into a plant; and
 d. optionally selecting a plant that contains the desired single locus conversion The skilled person is familiar with various techniques for genetically transforming a single locus in a plant cell, or mutating said cells.

Any pest or disease resistance genes may be introduced into a plant according to the invention, i.e. NUN 68106 MEM, progeny of said variety or into a plant comprising all but 1, 2, or 3 or more of the morphological and physiological characteristics of NUN 68106 MEM (e.g. as listed in Table 1). Resistance to one or more of the following diseases or pests is preferably introduced into plants of the invention: Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* f sp. *melonis* (Fom) race 0, *Fusarium oxysporum* fsp. *melonis* (Fom) race 1, *Fusarium oxysporum* f sp. *melonis* (Fom) race 2, *Fusarium oxysporum* fsp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and Melon Leafminer. Other resistances, against pathogenic viruses, fungi, bacteria, nematodes, insects or other pests may also be introduced, or other traits such as Melon Yellowing associated Virus (MYaV) resistance and Whitefly resistance.

Thus, invention also provides a method for developing a melon plant in a melon breeding program, using a melon plant of the invention, or its parts as a source of plant breeding material. Suitable plant breeding techniques are recurrent selection, backcrossing, pedigree breeding, mass selection, mutation breeding and/or genetic marker enhanced selection. For example, in one aspect, the method comprises crossing NUN 68106 MEM or progeny of said variety, or a plant comprising all but 1, 2, or 3 or more of the morphological and physiological characteristics of NUN 68106 MEM (e.g. as listed in Table 1), with a different melon plant, and wherein one or more offspring of the crossing are subject to one or more plant breeding techniques selected from the group consisting of recurrent selection, backcrossing, pedigree breeding, mass selection, mutation breeding and genetic marker enhanced selection (see e.g. Martin et al. 2008, Australian Journal of Crop Science 1(2): 43-46). For breeding methods in general see Principles of Plant Genetics and Breeding, 2007, George Acquaah, Blackwell Publishing, ISBN-13: 978-1-4051-3646-4.

The invention also provides a melon plant comprising at least a first set of the chromosomes of melon variety NUN 68106 MEM, a sample of seed of said variety having been deposited under Accession Number NCIMB 42990; optionally further comprising a single locus conversion or a mutation, wherein said plant has essentially all of the morphological and physiological characteristics of the plant comprising at least a first set of the chromosomes of said variety. In another embodiment, this single locus conversion confers a trait selected from the group consisting of yield, storage properties, color, male sterility, herbicide tolerance, insect resistance, pest resistance, disease resistance, environmental stress tolerance, modified carbohydrate metabolism and modified protein metabolism.

In one embodiment, a plant according to the invention, i.e. NUN 68106 MEM may also be mutated (by e.g. irradiation, chemical mutagenesis, heat treatment, etc.) and mutated seeds or plants may be selected in order to change one or more characteristics of said variety. Methods such as TILLING may be applied to melon populations in order to identify mutants. Similarly, NUN 68106 MEM may be transformed and regenerated, whereby one or more chimeric genes are introduced into the variety or into a plant comprising all but 1, 2, 3, or more of the morphological and physiological characteristics (e.g. as listed in Table 1). Transformation can be carried out using standard methods, such as *Agrobacterium tumefaciens* mediated transformation or biolistics, followed by selection of the transformed cells and regeneration into plants. A desired trait (e.g. genes conferring pest or disease resistance, herbicide, fungicide or insecticide tolerance, etc.) can be introduced into NUN 68106 MEM, or progeny of said variety, by transforming said variety or progeny of said variety with a transgene that confers the desired trait, wherein the transformed plant retains all or all but one, two or three of the phenotypic and/or morphological and/or physiological characteristics of NUN 68106 MEM or the progeny of said variety and contains the desired trait.

The invention also provides a plant or a cell of a plant comprising a desired trait produced by mutating a plant of variety NUN 68106 MEM or a cell thereof and selecting a plant the desired trait, wherein the mutated plant retains all or all but one of the phenotypic and morphological characteristics of said variety, optionally as described in Table 1, and contains the desired trait and wherein a representative sample of seed of variety NUN 68106 MEM has been deposited under Accession Number NCIMB 42990. In a further embodiment, the desired trait is selected from the group consisting of yield, fruit quality, male sterility, herbicide tolerance, insect resistance, pest resistance, disease resistance, environmental stress tolerance, modified carbohydrate metabolism, modified protein metabolism and ripening.

A suitable method for inducing mutation in NUN 68106 MEM comprises the steps of:
 a. Exposing a seed, a plant or a plant part or a cell of NUN 68106 MEM to a mutagenic compound or to radiation, wherein a representative sample of seed of NUN 68106 MEM is deposited under Accession Number NCIMB 42990, b. Selecting a seed, a plant or a plant part or a cell of NUN 68106 MEM having a mutation
c. Optionally growing and/or multiplying the seed, plant or plant part or cell of NUN 68106 MEM having the mutation.

The invention also provides a plant having one, two or three physiological and/or morphological characteristics which are different from those of NUN 68106 MEM and which otherwise has all the physiological and morphological characteristics of said variety, wherein a representative sample of seed of variety NUN 68106 MEM has been deposited under Accession Number NCIMB 42990. In particular variants which differ from NUN 68106 MEM in none, one, two or three of the characteristics mentioned in Table 1 are encompassed.

A part of a variety of the invention, i.e. NUN 68106 MEM (or of progeny of said varieties or of a plant having all physiological and/or morphological characteristics but one, two or three which are different from those of said variety) encompasses any cells, tissues, organs obtainable from the seedlings or plants, such as but not limited to: a melon fruit or a part thereof, a cutting, hypocotyl, cotyledon, seed coat, pollen and the like. Such parts can be stored and/or processed further. Encompassed are therefore also food or feed products comprising a part of NUN 68106 MEM or a part of progeny of said varieties, or a part of a plant having all but one, two or three physiological and/or morphological characteristics of NUN 68106 MEM, comprising one or more of such parts, optionally processed (such as canned, chopped, cooked, roasted, in a sauce, in a sandwich, pasted, puréed or concentrated, juiced, frozen, dried, pickled, or powdered).

In one aspect a haploid plant and/or a doubled haploid plant of NUN 68106 MEM, or of a plant having all but one, two or three physiological and/or morphological characteristics of NUN 68106 MEM, or progeny of any of these, is encompassed herein. Haploid and doubled haploid (DH) plants can, for example, be produced by cell or tissue culture and chromosome doubling agents and regeneration into a whole plant. For DH production chromosome doubling may be induced using known methods, such as colchicine treatment or the like.

In yet another aspect haploid plants and/or doubled haploid plants derived from NUN 68106 MEM that, when combined, make a set of parents of NUN 68106 MEM are encompassed herein. Thus the haploid plant and/or the doubled haploid plant of NUN 68106 MEM can be used in a method for generating parental lines of NUN 68106 MEM.

Using methods known in the art like "reverse synthesis of breeding lines" or "reverse breeding", it is possible to produce parental lines for a hybrid plant such as NUN 68106 MEM; where normally the hybrid is produced from the parental lines. Thus, this method introduces a tool that was not available in traditional breeding: a skilled person can take any individual heterozygous plant (called a "phenotypically superior plant" in Example 2 of WO2014076249; NUN 68106 MEM is such a plant) and generate a combination of parental lines (reverse breeding parental lines) that, when crossed, produce the variety NUN 68106 MEM. It is not necessary that the reverse breeding parental lines are identical to the original parental lines. Such new breeding methods are based on the segregation of individual alleles in the spores produced by a desired plant and/or in the progeny derived from the self-pollination of that desired plant, and on the subsequent identification of suitable progeny plants in one generation, or in a limited number of inbred cycles. Such a method is known from WO2014076249 or from Wijnker et al., Nature Protocols Volume: 9, Pages: 761-772 (2014) DOI: doi:10.1038/nprot.2014.049, which are enclosed by reference. Such method for producing parental lines for a hybrid organism, comprises the steps of: a) defining a set of genetic markers that are present in a heterozygous form (H) in a partially heterozygous starting organism; b) producing doubled haploid lines from spores of the starting organism: c) genetically characterizing the doubled haploid lines thus obtained for the said set of genetic markers to determine whether they are present in a first homozygous form (A) or in a second homozygous form (B); d) selecting at least one pair of doubled haploid lines that have complementary alleles for at least a subset of the genetic markers, wherein each member of the pair is suitable as a parental line for a hybrid organism.

Thus in one aspect, the invention relates to a method of producing a combination of parental lines of a plant of the invention (NUN 68106 MEM) comprising the step of making doubled haploid cells from haploid cells from said plant or a seed of that plant; and optionally crossing these parental lines to produce and collect seeds. In another aspect, the invention relates to a combination of parental lines produced by this method. In still another aspect said combination of parental lines can be used to produce a seed or plant of NUN 68106 MEM when these parental lines are crossed. In still another aspect, the invention relates to a combination of parental lines from which a seed or plant having all physiological and/or morphological characteristics of NUN 68106 MEM (when the characteristics are determined at the 5% significance level for plants grown under the same conditions).

In another aspect, the invention comprises a method for making doubled haploid cells from haploid cells of NUN 68106 MEM according to various methods known to the skilled person. A suitable method is colchicine treatment.

In another alternative aspect, the invention provides a method of introducing a single locus conversion or single trait conversion or a desired trait into NUN 68106 MEM comprising:
a. obtain a combination of a parental lines of NUN 68106 MEM, optionally through reverse synthesis of breeding lines,
b. introduce a single locus conversion in at least one of the parents of step a;
c. crossing the converted parent with the other parent of step a to obtain seed of NUN 68106 MEM A combination of a male and a female parental line of NUN 68106 MEM can be generated by methods described herein, for example through reverse synthesis of breeding lines.

In an embodiment of the invention, Step b) of the above method—introduce a single locus conversion in at least one of the parents of step a—may be done through the following method:
i. obtaining a cell or tissue culture of cells of the parental line of NUN 68106 MEM;
ii. genetically transforming or mutating said cells;
iii. growing the cells into a plant; and
iv. optionally selecting plants that contain the single locus conversion, the single trait conversion or the desired trait.

In another embodiment of the invention, Step b) of the above method—introduce a single locus conversion in at least one of the parents of step a—may also be done through the following method:
i. crossing the parental line of NUN 68106 MEM with a second melon plant comprising the single locus conversion, the single trait conversion or the desired trait;

ii. selecting F1 progeny plants that contain the single locus conversion, the single trait conversion or the desired trait;
iii. crossing said selected progeny plants of step ii with the parental line of step i, to produce a backcross progeny plant;
iv. selecting backcross progeny plants comprising the single locus conversion, the single trait conversion or the desired trait and otherwise all or all but one, two or three of the morphological and physiological characteristics the parental line of step i to produce selected backcross progeny plants; and
v. optionally repeating steps iii and iv one or more times in succession to produce selected second, third or fourth or higher backcross progeny plants comprising the single locus conversion, the single trait conversion or the desired trait and otherwise all or all but one, two or three of the morphological and physiological characteristics the parental line of step i to produce selected backcross progeny plants, when grown in the same environmental conditions.

The invention further relates to plants obtained by this method.

The above method is provided, wherein the single locus conversion concerns a trait, wherein the trait is yield or pest resistance or disease resistance. In one embodiment the trait is disease resistance and the resistance is conferred to Bacterial Wilt, Root Rot, Crown Blight, Melon Rust, Powdery Mildew, Verticillum Wilt, Sulphur Burn, Scab, Watermelon Mosaic, Downy Mildew, *Fusarium oxysporum* fsp. *melonis* (Fom) race 0, *Fusarium oxysporum* fsp. *melonis* (Fom) race 1, *Fusarium oxysporum* fsp. *melonis* (Fom) race 2, *Fusarium oxysporum* fsp. *melonis* (Fom) race 1-2, *Fusarium* Wilt R2, Anthracnose, Cucumber Mosaic, Squash Mosaic, Root Knot (Nematode), Aphid, Pickle Worm, Darkling Ground Beetle, Banded Cucumber Beetle, Mite, Western Spotted Cucumber Beetle, Melon Leafhopper, Melon Worm, Western Striped Cucumber Beetle and Melon Leafminer. Other resistances, against pathogenic viruses, fungi, bacteria, nematodes, insects or other pests may also be introduced, or other traits such as Melon Yellowing associated Virus (MYaV) resistance and Whitefly resistance.

Thus, the invention also provides a combination of parental lines which, when crossed, produce a seed or plant having all physiological and/or morphological characteristics of NUN 68106 MEM but one, two or three which are different (when grown under the same environmental conditions), as well as a seed or plant having all physiological and/or morphological characteristics of NUN 68106 MEM but one, two or three which are different (when the characteristics are determined at the 5% significance level for plants grown under the same conditions).

Also provided is a plant part obtainable from variety NUN 68106 MEM or from progeny of said variety or from a plant having all but one, two or three physiological and/or morphological characteristics which are different from those of NUN 68106 MEM, or from a vegetatively propagated plant of NUN 68106 MEM (or from its progeny or from a plant having all or all but one, two or three physiological and/or morphological characteristics which are different from those of NUN 68106 MEM), being selected from the group consisting of a fruit, a harvested fruit, a part of a fruit, a leaf, a part of a leaf, pollen, an ovule, a cell, a petiole, a shoot or a part thereof, a stem or a part thereof, a root or a part thereof, a root tip, a cutting, a seed, a part of a seed, seed-coat or another maternal tissue which is part of a seed grown on NUN 68106 MEM, or hypocotyl, cotyledon, a scion, a stock, a rootstock, a pistil, an anther, and a flower or a part thereof.

In still yet another aspect, the invention provides a method of determining the genotype of a plant of the invention comprising the step of detecting in the genome (e.g., a sample of nucleic acids) of the plant at least a first polymorphism or an allele. The skilled person is familiar with many suitable methods of genotyping, detecting a polymorphism or detecting an allele including restriction fragment length polymorphism identification (RFLP) of genomic DNA, random amplified polymorphic detection (RAPD) of genomic DNA, amplified fragment length polymorphism detection (AFLP), polymerase chain reaction (PCR), DNA sequencing, allele specific oligonucleotide (ASO) probes, and hybridization to DNA microarrays or beads. Alternatively, the entire genome could be sequenced. The method may, in certain embodiments, comprise detecting a plurality of polymorphisms in the genome of the plant, for example by obtaining a sample of nucleic acid from a plant and detecting in said nucleic acids a plurality of polymorphisms. The method may further comprise storing the results of the step of detecting the plurality of polymorphisms on a computer readable medium The invention also provides for a food or feed product comprising or consisting of a plant part described herein wherein the plant part can be identified as a part of the plant of the invention. Preferably, the plant part is a melon fruit or part thereof and/or an extract from a fruit or another plant part described herein. The food or feed product may be fresh or processed, e.g., dried, grinded, powdered, pickled, chopped, cooked, roasted, in a sauce, in a sandwich, pasted, puréed or concentrated, juiced, pickled, canned, steamed, boiled, fried, blanched and/or frozen, etc.

Marketable melon fruits are generally sorted by size and quality after harvest. Alternatively the melon fruits can be sorted by expected shelf life, pH or Brix.

Melons may also be grown for use as rootstocks (stocks) or scions (cions). Typically, different types of melons are grafted to enhance disease resistance, which is usually conferred by the rootstock, while retaining the horticultural qualities usually conferred by the scion. It is not uncommon for grafting to occur between cultivated melon varieties and related melon species. Methods of grafting and vegetative propagation are well-known in the art.

So in one aspect the invention relates to a plant comprising a rootstock or scion of NUN 68106 MEM.

All documents (e.g., patent publications) are herein incorporated by reference in their entirety. Cited references:
Acquaah, Principles of Plant Genetics and Breeding, 2007, Blackwell Publishing, ISBN-13: 978-1-4051-3646-4.
Colijn-Hooymans (1994), Plant Cell, Tissue and Organ Culture 39: 211-217).
Martin et al. 2008, Australian Journal of Crop Science 1(2): 43-46).
Parvathaneni et al., J. Crop Sci. Biotech. 2011 (March) 14 (1): 39~43
Ren et al., In Vitro Cell. Dev. Biol.-Plant (2013) 49:223-229;
Vos et al. 1995, Nucleic Acid Research 23: 4407-4414
Wijnker et al., Nature Protocols Volume: 9, Pages: 761-772 (2014) DOI: doi:10.1038/nprot.2014.049
WO2013182646
WO2014076249
WO2015136532
WO2016016855
WO2016120438

"Guidelines for the Conduct of Tests for Distinctness, Uniformity and Stability, TG104/5 (Geneva, as last revised in 2014 UPOV (International Union for the Protection of New Varieties and Plants, available on the world wide web at upov.int)
OBJECTIVE DESCRIPTION OF VARIETY—Muskmelon/Cantaloupe (*Cucumis melo* L.)" US Department of Agriculture, Agricultural Marketing Service, Plant Variety Protection Office

EXAMPLES

Development of NUN 68106 MEM

The hybrid NUN 68106 MEM was developed from a male and female proprietary inbred line of Nunhems. The female and male parents were crossed to produce hybrid (F1) seeds of NUN 68106 MEM The seeds of NUN 68106 MEM can be grown to produce hybrid plants and parts thereof (e.g. melon fruit). The hybrid NUN 68106 MEM can be propagated by seeds or vegetative.

The hybrid variety is uniform and genetically stable. This has been established through evaluation of horticultural characteristics. Several hybrid seed production events resulted in no observable deviation in genetic stability. Coupled with the confirmation of genetic stability of the female and male parents the Applicant has concluded that NUN 68106 MEM is uniform and stable.

Deposit Information

A total of 2500 seeds of the hybrid variety NUN 68106 MEM will be deposited according to the Budapest Treaty by Nunhems B.V. on Mar. 22, 2018, at the NCIMB Ltd., Ferguson Building, Craibstone Estate, Bucksburn, Aberdeen AB21 9YA, United Kingdom (NCIMB). The deposit will be assigned NCIMB number 42990. A deposit of NUN 68106 MEM and of the male and female parent line is also maintained at Nunhems B.V.

Access to the deposits will be available during the pendency of this application to persons determined by the Director of the U.S. Patent Office to be entitled thereto upon request. Subject to 37 C.F.R. § 1.808(b), all restrictions imposed by the depositor on the availability to the public of the deposited material will be irrevocably removed upon the granting of the patent. The deposit will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The most similar variety to NUN 68106 MEM is referred to as Reference Variety, a variety from Syngenta with the commercial name Jimenado F1.

Several trials comprising dozens of plants were conducted. For numerical characteristics averages will be calculated. For non-numerical characteristics the type/degree will be determined. In Table 1 the UPOV descriptors of NUN 68106 MEM (this application) are listed, which are average types based on several trials.

In accordance with one aspect of the present invention, there is provided a plant having the physiological and morphological characteristics of NUN 68106 MEM as presented in Table 1.

TABLE 1

| UPOV characteristic | NUN 68106 MEM |
|---|---|
| Seedling: length of hypocotyl; 1 very short/3 short/5 medium/7 long/9 very long | 5 |
| Seedling: size of cotyledon; 1 very small/3 short/5 medium/7 large/9 very large | 5 |
| Seedling: intensity of green color of cotyledon; 3 light/5 medium/7 dark | 5 |
| Leaf blade: size; 3 small/5 medium/7 large | 5 |
| Leaf blade: intensity of green color; 3 light/5 medium/7 dark | 5 |
| Leaf blade: development of lobes; 3 weak/5 medium/7 strong | 5 |
| Leaf blade: length of terminal lobe; 3 short/5 medium/7 long | 5 |
| Leaf blade: dentation of margin; 3 weak/5 medium/7 strong | 3 |
| Leaf blade: blistering; 3 weak/5 medium/7 strong | 5 |
| Petiole: attitude; 1 erect/2 semi-erect/3 horizontal | 2 |
| Petiole: length; 3 short/5 medium/7 long | 7 |
| Inflorescence: sex expression (at full flowering); 1 monoecious/2 andromonoecious | 2 |
| System of reproduction; 1 sexual/2 asexual | 1 |
| Young fruit: hue of green color of skin; 1 whitish green/2 yellowish green/green/4 greyish green | 3 |
| Young fruit: intensity of green color of skin; 1 very light/3 light/5 medium/7 dark/9 very dark | 7 |
| Young fruit: density of dots; 1 absent or very sparse/3 sparse/5 medium/7 dense/9 very dense | 5 |
| Young fruit: size of dots; 3 small/5 medium/7 large | 3 |
| Young fruit: contrast of dot color/ground color; 3 weak/5 medium/7 strong | 5 |
| Young fruit: conspicuousness of groove coloring; 1 absent or very weak/3 weak/5 medium/7 strong/9 very strong | 1 |
| Young fruit: length of peduncle; 3 short/5 medium/7 long | 5 |
| Young fruit: thickness of peduncle 1 cm from fruit; 3 thin/5 medium/7 thick | 5 |
| Young fruit: extension of darker area around peduncle; 1 absent or very small/3 small/5 medium/7 large | 3 |
| Fruit: change of skin color from young fruit to maturity; 1 early in fruitdevelopment/2 late in fruit development/3 very late in fruit development or no change | 3 |
| Fruit: length; 1 very short/3 short/5 medium/7 long/9 very long | 7 |
| Fruit: diameter; 1 very narrow/3 narrow/5 medium/7 broad/9 very broad | 7 |
| Fruit: ratio lenght/diameter; 1 very small/2 very small to small/3 small/4 small to medium/5 medium/6 medium to large/7 large/8 large to very large/9 very large | 6 |
| Fruit: position of maximum diameter; 1 toward stem end/2 at middle/3 toward blossom end | 2 |
| Fruit: weight (kg) | 4.4 |
| Fruit: shape in longitudinal section; 1 ovate/2 medium elliptic/3 broad elliptic/4 circular/5 quadrangular/6 oblate/7 obovate/8 elongated | 2 |
| Fruit: shape in longitudinal section; 1 flattened/2 round/3 egg shaped/4 elliptic/5 elongated | 4 |
| Fruit: ground color of skin; 1 white/2 yellow/3 green/4 grey | 3 |
| Fruit: ground color of skin; 1 white/2 yellow/3 yellowish green/4 green/5 ochre | 4 |
| Fruit: intensity of ground color of skin; 3 light/5 medium/7 dark | 7 |
| Fruit: secondary colour of skin; 1 absent/9 present | 9 |
| Fruit: distribution of secondary color of skin; 1 in dots/2 in spots/3 in dots and in spots | 3 |
| Fruit: hue of ground color of skin; 1 absent or very weak/2 whitish/3 yellowish/4 orange/5 ochre/6 greenish/7 greyish | 1 |
| Fruit: density of dots; 1 absent or very sparse/3 sparse/5 medium/7 dense/9 very dense | 7 |
| Fruit: size of dots; 3 small/5 medium/7 large | 3 |
| Fruit: color of dots; 1 white /2 yellow/3 green | 2 |
| Fruit: intensity of color of dots; 3 light/5 medium/7 dark | 5 |
| Fruit: density of patches; 1 absent or very sparse/3 sparse/5 medium/7 dense/9 very dense | 3 |
| Fruit: size of patches; 3 small/5 medium/7 large | 3 |
| Fruit: warts; 1 absent/9 present | 1 |
| Peduncle: abscission layer; 1 absent/9 present | 1 |
| Fruit: strength of attachment of peduncle at maturity; 1 very weak/3 weak/5 medium/7 strong/9 very strong | 7 |
| Fruit: shape of base; 1 pointed/2 rounded/3 truncate | 2 |
| Fruit: shape of apex; 1 pointed/2 rounded/3 truncate | 2 |
| Fruit: size of pistil scar; 3 small/5 medium/7 large | 3 |
| Fruit: grooves; 1 absent or very weak expressed/2 weakly expressed/3 strongly expressed | 1 |

TABLE 1-continued

| UPOV characteristic | NUN 68106 MEM |
|---|---|
| Fruit: creasing of surface; 1 absent or very weak/3 weak/5 medium/ 7 strong/9 very strong | 3 |
| Fruit: cork formation; 1 absent/9 present | 9 |
| Fruit: thickness of cork layer; 1 very thin/3 thin/5 medium/ 7 thick/9 very thick | 3 |
| Fruit: pattern of cork formation; 1 dots only/2 dots and linear/ 3 linear only/4 linear and netted/5 netted only | 3 |
| Fruit: pattern of cork formation; 3 in dots/5 linear/7 netted | 5 |
| Fruit: density of pattern of cork formation; 1 very sparse/3 sparse/ 5 medium/7 dense/9 very dense | 5 |
| Thickness of epidermis; 3 thin/5 medium/7 thick | 5 |
| Fruit: rate of skin color change from maturity to over maturity; 1 absent or very slow/3 slow/5 medium/7 fast | 1 |
| Fruit: width of flesh in longitudinal section (at maximum fruit diameter); 3 thin/5 medium/7 thick | 7 |
| Fruit main color of flesh; 1 white/2 greenish white/3 green/ 4 yellowish white/5 orange/6 reddish orange | 1 |
| Fruit: intensity of color of flesh; 3 light/5 medium/7 dark | 3 |
| Fruit: color of flesh in outer zone; 1 creme/5 green/7 orange | 1 |
| Fruit: secondary salmon coloring of flesh; 1 absent or very weak/ 3 weak/5 medium/7 strong/9 very strong | 5 |
| Fruit: firmness of flesh; 3 soft/5 medium/7 firm | 5 |
| Fruit: at over maturity: hue of color of skin; 1 yellow/2 orangish yellow/3 creamish | 1 |
| Fruit at over maturity: intensity of yellow color of skin; 3 light/ 5 medium/7 dark | 5 |
| Shape of Placental cavity (in transverse section); 1 circular/ 2 triangular | 2 |
| Seed: size; 3 small/5 medium/7 large | 7 |
| Seed: length; 1 very short/3 short/5 medium/7 long/9 very long | 7 |
| Seed: width; 1 very narrow/3 narrow/5 medium/7 broad/9 very broad | 5 |
| Seed: shape; 1 not pine-nut shape/2 pine-nut shape | 1 |
| Seed: color; 1 whitish/2 cream yellow | 2 |
| Seed: intensity of cream yellow color; 3 light/5 medium/7 dark | 5 |
| Time of male flowering; 3 early/5 medium/7 late | 5 |
| Time of female flowering; 3 early/5 medium/7 late | 5 |
| Time of ripening /maturity; 1 very early/3 early/5 medium/7 late/ 9 very late | 5 |
| Shelf life of fruit; 1 very short/3 short/5 medium/7 long/9 very long | 7 |

Table 1, 2 and 3 contain typical values. Values may vary due to environment. Other values that are substantially equivalent are also within the scope of the invention. N.A.=not applicable; n.r.=not recorded.

What is claimed is:

1. A plant, plant part or seed of melon variety NUN 68106 MEM, wherein a representative sample of seed of said melon variety is deposited under Accession Number NCIMB 42990.

2. The plant part of claim 1, wherein the plant part is a leaf, pollen, an ovule, a fruit, a scion, a root, a rootstock, cutting, a flower or a cell.

3. A seed that produces the plant of claim 1.

4. A seed grown on the plant of claim 1, wherein a plant grown from said seed does not differ from the plant of claim 1 when the characteristics are determined at the 5% significance level when grown under the same environmental conditions.

5. A melon plant or a part thereof derived from the plant of claim 1 which does not differ from the plant of claim 1 in all of the characteristics of Table 1, when the characteristics are determined at the 5% significance level for plants grown under the same environmental conditions, and wherein a representative sample of seed of said melon variety has been deposited under Accession Number NCIMB 42290.

6. A melon plant or a part thereof derived from the plant of claim 1 which does not differ from the plant of claim 1, when the characteristics are determined at the 5% significance level when grown under the same environmental conditions, wherein a representative sample of seed of said melon variety has been deposited under Accession Number NCIMB 42290.

7. A tissue or cell culture comprising cells of the plant of claim 1.

8. The tissue or cell culture according to claim 7, comprising cells or protoplasts derived from a plant part, wherein the plant part is an embryo, a meristem, a cotyledon, a hypocotyl, pollen, a leaf, an anther, a root, a root tip, a pistil, a petiole, a flower, a fruit, a seed, a stem or a stalk.

9. A melon plant regenerated from the tissue or cell culture of claim 7, wherein the plant has all of the physiological and morphological characteristics of the plant of melon variety NUN 68106 MEM, when the characteristics are determined at the 5% significance level for plants grown under the same environmental conditions, and wherein a representative sample of seed of melon variety NUN 68106 MEM is deposited under Accession Number NCIMB 42990.

10. A method of producing the plant of claim 1 or a part thereof, said method comprising vegetative propagation of at least a part of the plant of melon variety NUN 68106 MEM, wherein a representative sample of seed of said melon variety is deposited under Accession Number NCIMB 42990.

11. The method of claim 10, wherein said vegetative propagation comprises regenerating a whole plant from said part of the plant of melon variety NUN 68106 MEM, wherein a representative sample of seed of said melon variety is deposited under Accession Number NCIMB 42990.

12. The method of claim 10, wherein said part is a cutting, a cell culture or a tissue culture.

13. A vegetative propagated plant of claim 1 or a part thereof, wherein the vegetative propagated plant has all of the physiological and morphological characteristics of the plant of NUN 68106 MEM, when the characteristics are determined at the 5% significance level for plants grown under the same environmental conditions, and wherein a representative sample of seed of melon variety NUN 68106 MEM is deposited under Accession Number NCIMB 42990.

14. A method of producing a melon plant, comprising crossing the plant of claim 1 with a second melon plant at least once, and selecting a progeny melon plant from said crossing and optionally allowing the progeny to form seed.

15. A first generation progeny plant of the plant of claim 1 obtained by selfing or cross-pollinating the plant of claim 1 with another melon plant, wherein said progeny plant has all of the physiological and morphological characteristics of the plant of melon variety NUN 68106 MEM, wherein a representative sample of seed of said melon variety is deposited under Accession Number NCIMB 42990, when said characteristics are determined at the 5% significance level for plants grown under the same environmental conditions.

16. A melon plant derived from the plant of claim 1 having one physiological or morphological characteristic which is different from those of the plant of claim 1, and which otherwise has all the physiological and morphological characteristics of the plant of claim 1, when determined at the 5% significance level for plants grown under the same environmental conditions, and wherein a representative sample of seed of said melon variety has been deposited under Accession Number NCIMB 42290.

17. The plant of claim 1 further comprising a single locus conversion, wherein said plant has all of the morphological and physiological characteristics of the plant of melon variety NUN 68106 MEM, wherein a representative sample of seed of said melon variety is deposited under Accession Number NCIMB 42990, when said characteristics are determined at the 5% significance level for plants grown under the same environmental conditions, optionally wherein the single locus conversion confers a trait of male sterility, herbicide tolerance, insect resistance, pest resistance, disease resistance, environmental stress tolerance, modified carbohydrate metabolism or modified protein metabolism.

18. A method of producing double haploids of the plant of claim 1 comprising making doubled haploid cells from haploid cells from the plant or seed of melon variety NUN 68106 MEM wherein a representative sample of seed of melon variety NUN 68106 MEM is deposited under Accession Number NCIMB 42990.

19. A method of grafting the scion or rootstock of the plant of melon variety NUN 68106 MEM, said method comprising attaching tissue from the scion or rootstock of claim 2 to the tissue of a second plant, and optionally regenerating a plant therefrom.

20. A container comprising the plant, plant part or seed of claim 1.

21. A food, a feed product or a processed product comprising the plant part of claim 2, wherein the plant part is a fruit or a part thereof.

22. A method of producing a melon fruit, comprising:
   a. growing the plant of claim 1 until it sets at least one fruit; and
   b. collecting at least one fruit.

23. A method of collecting pollen of melon variety NUN 68106 MEM comprising:
   a. growing the plant of claim 1 until at least one flower contains pollen; and
   b. collecting the pollen.

24. A method of producing a melon plant with a desired trait, comprising mutating a melon plant of variety NUN 68106 MEM and selecting a mutated plant with a desired trait, wherein the mutated plant retains all of the physiological and morphological characteristics of melon variety NUN 68106 MEM, when the characteristics are determined at the 5% significance level for plants grown under the same environmental conditions, and wherein a representative sample of seed of said melon variety is deposited under Accession Number NCIMB 42990, and wherein the desired trait is male sterility, herbicide tolerance, pest resistance, environmental stress resistance, modified carbohydrate metabolism, modified protein metabolism or ripening.

* * * * *